(12) United States Patent
Yang et al.

(10) Patent No.: US 8,956,592 B2
(45) Date of Patent: Feb. 17, 2015

(54) ORAL CARE COMPOSITIONS

(75) Inventors: Ying Yang, Monmouth Junction, NJ (US); Shyamala Pillai, Piscataway, NJ (US); Lin Fei, Kendall Park, NJ (US); Ravi Subramanyam, Mumbai (IN); Guofeng Xu, Plainsboro, NJ (US)

(73) Assignee: Colgate-Palmolive Company, New York, NY (US)

( * ) Notice: Subject to any disclaimer, the term of this patent is extended or adjusted under 35 U.S.C. 154(b) by 24 days.

(21) Appl. No.: 13/577,621

(22) PCT Filed: Feb. 24, 2011

(86) PCT No.: PCT/US2011/026019
§ 371 (c)(1),
(2), (4) Date: Aug. 7, 2012

(87) PCT Pub. No.: WO2011/106493
PCT Pub. Date: Sep. 1, 2011

(65) Prior Publication Data
US 2012/0308489 A1  Dec. 6, 2012

Related U.S. Application Data

(60) Provisional application No. 61/307,673, filed on Feb. 24, 2010.

(51) Int. Cl.
*A61K 36/575* (2006.01)
*A61Q 11/00* (2006.01)
*A61K 8/34* (2006.01)
*A61K 8/86* (2006.01)

(52) U.S. Cl.
CPC ............... *A61Q 11/00* (2013.01); *A61K 8/347* (2013.01); *A61K 8/86* (2013.01); *A61K 2800/49* (2013.01)
USPC ................ 424/49; 424/725; 424/58; 424/769

(58) Field of Classification Search
CPC .. A61K 2300/00; A61K 36/575; A61K 11/00

USPC ..................................... 424/49, 725, 58, 769
See application file for complete search history.

(56) References Cited

U.S. PATENT DOCUMENTS

| | | | |
|---|---|---|---|
| 5,614,174 A | 3/1997 | Hsu et al. | |
| 6,544,409 B2 | 4/2003 | DeSouza | |
| 2006/0127329 A1 | 6/2006 | Xu et al. | |
| 2006/0134024 A1 | 6/2006 | Trivedi et al. | |
| 2006/0140880 A1* | 6/2006 | Subramanyam et al. | ....... 424/49 |
| 2006/0140885 A1 | 6/2006 | Gaffar et al. | |
| 2009/0087501 A1 | 4/2009 | Cummins | |

FOREIGN PATENT DOCUMENTS

| | | |
|---|---|---|
| CN | 1331968 | 1/2002 |
| JP | H07-033649 | 2/1995 |
| JP | 2003-532664 | 11/2003 |
| WO | WO 97/35599 | 10/1997 |
| WO | WO 01/82922 | 11/2001 |
| WO | WO 2004/000235 | 12/2003 |

OTHER PUBLICATIONS

Fordyce et al., "Studies on Reactions Relating to Carbohydrates and Polysaccharides. LVI. The Synthesis of the Higher Polyoxyethylene Glycols," J. Am. Chem. Soc., 1939, 61:1905-1910.
Patocka et al., "Expectations of biologically active compounds of the genus *Magnolia* in biomedicine," J. Appl. Biomed., 2006, pp. 171-178, vol. 4, No. 4.
Powell, "Chapter 18—Polyethylene Glycol," Handbook of Water-Soluble Gums and Resins, 1980, pp. 18/1-18/31, R.L. Davidson ed. (McGraw-Hill, New York).
International Search Report issued for International Application No. PCT/US2011/026017 mailed on May 24, 2011.
International Search Report and Written Opinion for International Application No. PCT/US2011/026019 mailed Oct. 31, 2013.

* cited by examiner

*Primary Examiner* — Frederick Krass
*Assistant Examiner* — Tracy Liu
(74) *Attorney, Agent, or Firm* — Anne Louise St. Martin

(57) ABSTRACT

Disclosed herein are methods of enhancing the solubility and delivery of one or more active ingredients found in magnolia extract, or a synthetic analog thereof, in an oral composition.

3 Claims, No Drawings

ORAL CARE COMPOSITIONS

CROSS REFERENCE TO RELATED APPLICATIONS

This application is a national stage entry under 35 U.S.C. §371 of International Patent Application No. PCT/US2011/026019, filed on Feb. 24, 2011, which claims priority to U.S. Provisional Patent Application No. 61/307,673, filed on Feb. 24, 2010, which are hereby incorporated by reference in their entirety.

BACKGROUND

There is often an undesired interaction between the active ingredients of magnolia extract, or synthetic analogues thereof, and components of the delivery vehicles used to formulate conventional oral compositions of magnolia extract that reduces the effective performance of such oral compositions. Consequently, there exists a need to enhance the solubility and positive interaction of the one or more active ingredients of magnolia extract, or synthetic analogues thereof, with other components in oral compositions. There also exists a need to enhance the delivery of the one or more active ingredients of magnolia extract or their synthetic analogues, in oral compositions.

SUMMARY

Some embodiments of the present invention provide a method of enhancing the solubility of at least one of the one or more active ingredients found in magnolia extract, or a synthetic analogue thereof, comprising admixing polyethylene glycol with at least one of the one or more active ingredients, or said synthetic analogue thereof. In some embodiments, at least one of the one or more active ingredients found in magnolia extract is selected from: magnolol; honokiol; tetrahydromagnolol (5,5'-dipropylbiphenyl-2,2'-diol); tetrahydrohonokiol (3',5-dipropylbiphenyl-2,4'-diol); n-butyl magnolol (5,5'-dibutylbiphenyl-2,2'-diol). In some embodiments, said synthetic analogue thereof is selected from: isopropyl magnolol; isobutyl magnolol; and dichloromagnolol.

In other embodiments, the invention provides an oral composition comprising at least one of the one or more active ingredients found in magnolia extract, or a synthetic analogue thereof; polyethylene glycol; and an orally acceptable carrier.

Some embodiments provide an oral composition comprising: about 0.05 to about 10% by weight polyethylene glycol; about 0.05 to about 5% by weight of at least one of the one or more active ingredients found in magnolia extract or a synthetic analogue thereof.

Further embodiments provide a method of treating or preventing a condition of the oral cavity comprising: providing a composition comprising: from about 0.05 to about 10% by weight polyethylene glycol; from about 0.05 to about 5% by weight of one or more active ingredients found in magnolia extract or a synthetic analogue thereof; and an orally acceptable carrier; and applying the composition to the oral cavity of a subject in need thereof.

In some embodiments, the composition is applied to the oral cavity daily for a period of one week. In some embodiments, the composition is applied to the oral cavity for up to 2 weeks. In some embodiments, the composition is applied to the oral cavity for a period lasting more than 2 weeks.

DETAILED DESCRIPTION

The methods and compositions of the present embodiments impart advantages over the prior art compositions by providing an oral composition that is well solubilized, safe, and highly efficacious against bacterial infection and/or inflammation in a mammalian subject.

Each reference cited herein is hereby incorporated by reference in its entirety.

The expressions "carrier" or "aqueous carrier" or "orally acceptable carrier" as used throughout this description denote any safe and effective materials for use herein. Such materials include, water, solvents, etc., that may contain a humectant such as glycerine, sorbitol, xylitol and the like. The carrier or orally acceptable carrier also may include additional dentifrice components, such as thickening agents, ionic active ingredients, buffering agents, anticalculus agents, abrasive polishing materials, peroxide sources, alkali metal bicarbonate salts, surfactants, titanium dioxide, coloring agents, flavor systems, sweetening agents, antimicrobial agents, herbal agents, desensitizing agents, stain reducing agents, and mixtures thereof.

All percentages and ratios used herein are by weight of the oral care composition, unless otherwise specified. All measurements are made at 25° C., unless otherwise specified.

Throughout this description and claims, the disclosure of a certain numerical value (e.g., temperature, weight percent of components, etc.) is meant to denote that value, plus or minus an additional value that would be understood by persons having ordinary skill in the art, depending on the variable and the degree of measurement error typically associated with that value. For example, a given temperature would be understood by a person having ordinary skill in the art to include up to 10% variability, given the instrument used to measure the temperature.

Some embodiments of the present invention provide a method for enhancing the solubility of at least one of the one or more active ingredients found in magnolia extract, or a synthetic analogue thereof, in an oral composition. In some embodiments, the method comprises admixing an effective amount of polyethylene glycol with at least one of the one or more of the active ingredients found in magnolia extract, or a synthetic analogue thereof. In some embodiments, the active ingredient is selected from: magnolol, honokiol, tetrahydromagnolol, tetrahydrohonokiol (3',5-dipropylbiphenyl-2,4'-diol), 5,5'-di-n-butyl-biphenyl-2,2'-diol, n-butyl magnolol (5,5'-dibutylbiphenyl-2,2'-diol). In some embodiments, the orally acceptable carrier does not contain polyethylene glycol as a humectant. In other embodiments, the orally acceptable carrier contains polyethylene glycol.

Some embodiments comprise a method of making a solubilized oral composition by mixing from about 0.05 to about 10% by weight polyethylene glycol with the one or more of the active ingredients found in magnolia extract or a synthetic analogue thereof; and an orally acceptable carrier. In some embodiments, the polyethylene glycol comprises from about 0.1 to about 5% by weight of the composition. In other embodiments, at least one of the one or more active ingredients found in magnolia extract, or a synthetic analogue thereof, is present in the amount of from about 0.05 to about 5% by weight of the composition, preferably from about 0.1 to about 3% by weight of the composition.

Further embodiments of the present invention provide an oral composition comprising: (i) an effective amount of polyethylene glycol; (ii) at least one of the one or more active ingredients found in magnolia extract, or a synthetic analogue thereof; and (iii) an orally acceptable carrier.

In some embodiments, the compositions are used to inhibit the excess production of cellular mediators of inflammation in oral tissues at sites of inflammation caused by infection, environmental toxins, or trauma in the oral cavity. In some embodiments, an effective amount of at least one of the one or more active ingredients found in magnolia extract, or a synthetic analogue thereof, reduces the levels or activity of proinflammatory mediators adequately to reduce the concentration in the mammalian subject to basal levels in the oral tissue of the subjects treated, without unnecessarily suppressing all intercellular mediator activity.

In some embodiments, at least one of the one or more active ingredients found in magnolia extract, or a synthetic analogue thereof, will be present in the amount required to have the desired therapeutic or prophylactic effect in the human or lower animal subject to whom the active is administered, without undue adverse side effects (such as toxicity, irritation, or allergic response), commensurate with a reasonable benefit/risk ratio when used in the manner of this invention. The specific safe and effective amount of the active ingredients will vary with such factors as the particular condition being treated, the physical condition of the subject, the nature of concurrent therapy (if any), the specific compound used, the specific dosage form, the carrier employed, and the desired dosage regimen. Those skilled in the art will be capable of determining a safe and effective amount of active ingredient to use in the compositions and methods, using the guidelines provided herein.

In highly sensitive tissue, high concentrations of magnolia may potentially cause irritation and exacerbate inflammation, rather than reduce it. While the potential for additional inflammation is dependent upon the individual subject's status and response to irritants, as well as other variables related to treatment, it is preferred that at least one of the one or more active ingredients found in magnolia extract is provided to the subject at a non-irritating concentration. By "non-irritating" it is meant that the contact of the oral composition with the oral cavity of a mammalian subject does not increase soreness, pain, redness, or roughness, nor does it exacerbate or worsen inflammation of the oral tissue.

In addition, the concentration of at least one of the one or more active ingredients found in magnolia extract, or synthetic analogue thereof, will vary depending on delivery form, dosage regimen, end benefits, pathology, and/or the individual therapeutic requirements of the subject(s) to whom it is admitted, and as such, it is contemplated that the amount of the one or more active ingredients found in magnolia extract may vary. Additionally, the concentration of the active ingredient is typically dependent upon the form of the oral composition. For example, mouthrinses typically have a relatively low concentration of an active ingredient, whereas dentifrices, gels, or toothpowders have a higher concentration to achieve the same delivered dosage based on ease of dispersion. Likewise, confectionary compositions typically have a relatively high concentration of active ingredient to enable sufficient dispersion as they dissolve or are masticated.

The term "confectionery composition" as used herein includes chewing gums, and orally dissolvable tablets, beads, and lozenges. Saliva dissolves the lozenge or chewable gum product, and promotes prolonged contact with oral surfaces so that the active ingredient in a lozenge, tablet, bead or chewing gum form is adequately delivered to the oral surface targeted, when the product is used.

As referred to herein, the expressions "extract of magnolia" or "magnolia extract" denote an extract from dried cortex, or bark, of a plant from the Magnoliaceae family, such as *Magnolia officinalis*, (hereinafter "magnolia"), or a synthetic or semi-synthetic equivalent of such an extract or an active component thereof. In some embodiments, the oral composition comprises an extract of magnolia. Preferably, extracts of Magnolia Cortex (the bark of *Magnolia officinalis*) contain active compounds including: magnolol, honokiol, tetrahydromagnolol (5,5'-dipropylbiphenyl-2,2'-diol), and tetrahydrohonokiol (3',5-dipropylbiphenyl-2,4'-diol), which have demonstrated bactericidal properties against representative oral bacteria *S. mutans, F. nucleatum, V. parvula, A. naslundii, P. gingivitis* in in vitro tests. It should be noted that any plant from the Magnoliaceae family is suitable for extracting the active ingredients used in the present embodiment.

In some embodiments, the magnolia extract contains an antimicrobially effective concentration of a compound selected from: magnolol, honokiol, tetrahydromagnolol, tetrahydrohonokiol (3',5-dipropylbiphenyl-2,4'-diol), and n-butyl magnolol (5,5'-dibutylbiphenyl-2,2'-diol), and a combination of two or more thereof. In other embodiments, the oral composition comprises one or more active ingredients selected from the group consisting of magnolia extract, magnolol, honokiol, tetrahydromagnolol, tetrahydrohonokiol (3', 5-dipropylbiphenyl-2,4'-diol), n-butyl magnolol (5,5'-dibutylbiphenyl-2,2'-diol), and a combination of two or more thereof; in an amount effective to treat bacterial and/or inflammation related oral conditions in a mammalian subject.

In some embodiments, the magnolia extract can be prepared by way of extraction. In one method of extraction, the dried, crushed Magnolia bark in the form of a powder is sequentially contacted with ethanol, methylene chloride, and cyclohexane to form in each step a concentrated paste, the last paste form being dissolved in heated petroleum ether at about 50°-60° C., and then dried under vacuum, the final extraction yielding an extract containing about 5 to about 10% by weight honokiol and about 15 to about 25% by weight magnolol.

In another method of extraction, the Magnolia extract is prepared from dried Magnolia plant bark and can be made by extracting the bark using an appropriate solvent. Preferred solvents include methanol, ethanol, methylene chloride, hexane cyclohexane, pentane, petroleum ether, chloroform, hydrochloric acid, ethylene dichloride, and hydrofluoroalkanes, such as 1,1,1,2-tetrafluoroethane or HFA-13A. Generally, one part of plant tissue (dry basis) is extracted with 5 to 50 parts, preferably 15 parts to 30 parts of solvent using an extraction apparatus where the solvent is contacted with the bark to obtain a concentrated paste which is then subjected to one or more additional extraction steps with different solvents to further concentrate the originally obtained paste over an extended period of time, preferably about 6 hours to about 1-2 days, more preferably for about 1 day. In one simplified method of extraction, the dried, crushed Magnolia bark in the form of a powder is contacted with a hydrofluoroalkane (such as, 1,1,1,2-tetrafluoroethane (HFA-13A)) to form a concentrated final extraction yielding an extract containing 5 to 50% honokiol and 5 to 50% magnolol.

In yet another method of extraction, the magnolia extract is isolated by supercritical fluid extraction (SFE) using carbon dioxide ($CO_2$). Supercritical fluids are gases with properties between that of a "normal" phase of gas and liquid. Pressure variations control the properties of the supercritical fluids, which can range from more gas-like behavior to more liquid-like behavior, depending on the application. Supercritical fluids use a solvent that is readily available, inexpensive, and environmentally safe ($CO_2$ and $H_2O$). Carbon dioxide is non-toxic, non-explosive, readily available and easily removed from the extracted products. Process temperatures for SFE are generally low to moderate. Thus, SFE produces nearly solvent-free products, and further avoid any potential deterioration reactions.

Additionally, natural contaminants that may be potentially present in other extraction methodologies are generally absent in the SFE extracted product. For example, compounds such as aristocholic acid and alkaloids, such as magnocurine and tubocurarine, are maintained at low concentrations (for example, generally less than 0.0002 percent). Thus, in the embodiment where the magnolia is extracted by SFE, the extract is substantially free from chemical alterations brought about by heat and water, from solvent residues, and other artifacts.

As used herein, "extracting" or "extraction" of a solid or liquid material means contacting the material with an appropriate material, such as a solvent to remove the substance(s) desired to be extracted from the material. Such an extraction may be carried out by conventional means known to one of skill in the art, for example, by using an extraction apparatus, such as a Soxhlet apparatus, which retains the solid material in a holder and allows the solvent to flow through the material; or by blending the solvent and material together and then separating the liquid and solid phases or two immiscible liquid phases, such as by filtration or by settling and decanting.

In various methods of extraction, the magnolia extract of the present invention may be comprised of magnolol from 2% to 95%. In some embodiments, the magnolol may be present in the extract from 5 to 50%. In other embodiments, magnolol may be present in the extract from 30 to 50%. In certain embodiments, the honokiol may be present in the extract from 2 to 95%. In further embodiments, the honokiol may be present in the extract from 5 to 50%. In yet other embodiments, honokiol may be present in the extract from 30 to 50%.

In certain embodiments, it is preferred that at least one of the one or more active ingredients found in magnolia extract comprise either magnolol, honokiol, or a combination thereof. Magnolol and honokiol are non-ionic hydroxybiphenyl compounds, the structures of which are represented as follows:

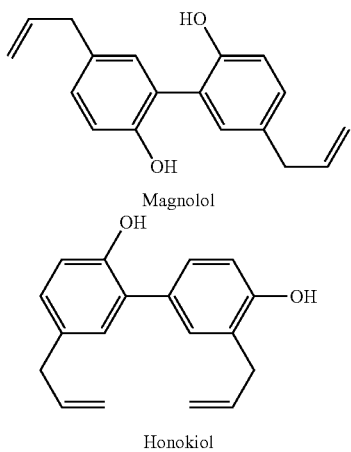

Magnolol

Honokiol

Additionally, tetrahydromagnolol (5,5'-dipropylbiphenyl-2,2'-diol) and tetrahydrohonokiol (3',5-dipropylbiphenyl-2,4'-diol) are hydrogenated analogues of magnolol and honokiol, respectively, and they are often found in the extracts of magnolia, and as such may be included in the oral composition. Furthermore, 5,5'-dibutylbiphenyl-2,2'-diol (homolog of magnolol), may be also included in the oral composition, and the synthesis of this compound can be achieved through conventional organic synthesis by a person of ordinary skill in the art. The structures of tetrahydromagnolol (5,5'-dipropyl-biphenyl-2,2'-diol), tetrahydrohonokiol (3',5-dipropylbiphenyl-2,4'-diol) and 5,5'-di-n-butylbiphenyl-2,2'-diol (homolog of magnolol) are shown below.

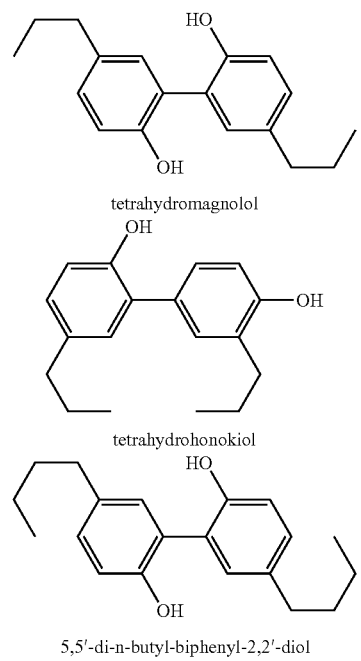

tetrahydromagnolol tetrahydrohonokiol 5,5'-di-n-butyl-biphenyl-2,2'-diol

Orally acceptable carriers for use in the invention include the conventional and known carriers used in making toothpastes, tooth powders, prophylaxis pastes, mouth rinses, lozenges, gums, beads, and the like, and are more fully described hereinafter. It is preferred that the orally acceptable carrier does not cause irritation, swelling or pain and does not typically produce an allergic or untoward reaction such as gastric upset, nausea or dizziness. Selection of specific carrier components is dependant on the desired product form, including dentifrices, toothpastes, tooth powders, prophylaxis pastes, mouth rinses, lozenges, gums, gels, paints, confectionaries, and the like.

The term "mouthrinse" in the present invention refers to oral compositions that are substantially liquid in character, such as a mouth wash, spray, or rinse. In such a preparation the orally acceptable carrier typically has an aqueous phase comprising water or a water and alcohol mixture. Further, in various embodiments, the oral carrier includes a humectant and surfactant as described below. Generally, the weight ratio of water to alcohol is in the range of in an amount of 1:1 to 20:1, preferably 3:1 to 10:1 and more preferably 4:1 to 6:1. The total amount of water-alcohol mixture in this type of preparation is typically in an amount of 70 to 99.9% of the preparation. In various embodiments, the alcohol is typically ethanol or isopropanol.

As recognized by one of skill in the art, the orally acceptable carrier of the present invention may also comprise a variety of other conventional active ingredients known to one of skill in the art, including anti-plaque agents, whitening agents, antibacterial agents, tartar control (anticalculus) agent, anti-caries agents, sensitivity agents, and the like. Preferably, the carrier does not substantially reduce the efficacy of the anti-inflammatory and antibacterial active ingredients found in magnolia extract or synthetic analogues thereof.

The pH of such liquid and other preparations of the oral composition of the present invention is generally in an amount of 4.5 to 10. The pH can be controlled with acid (e.g., citric acid or benzoic acid) or base (e.g., sodium hydroxide) or buffered (with sodium citrate, benzoate, carbonate, or bicarbonate, disodium hydrogen phosphate, or sodium dihydrogen phosphate, for example).

In various embodiments, the aqueous oral composition (e.g., mouthrinse) contains a humectant. The humectant is generally a mixture of humectants, such as glycerin and sorbitol, and a polyhydric alcohol such as hexylene glycol, or polyethylene glycol, although the use of polyethylene glycol as a humectant in addition to its use to enhance the solubility of the active ingredient is optional. The humectant content typically is in the range of 5 to 40% and preferably 10 to 30%. Surfactants useful in the present embodiment include anionic, nonionic, and zwitterionic surfactants. The surfactant usually is present in the aqueous oral compositions of the present invention in an amount of 0.01% to 5%, preferably in an amount of 0.5% to 2.5%.

The oral composition according to the present invention may optionally include other materials, such as for example, cleaning agents, flavouring agents, sweetening agents, adhesion agents, surfactants, foam modulators, abrasives, pH modifying agents, humectants, moisturizers, mouth feel agents, colorants, abrasives, preservatives, fluoride ion source, saliva stimulating agents, emollients, viscosity modifiers, diluents, emulsifiers, nutrients and combinations thereof. Various components that may be added to the oral composition include, for example, a sweetening agent such as saccharin, or sodium saccharin, alcohols such as ethanol, fluoride ion sources such as sodium fluoride, as well as glycerine, sorbitol, polyethylene glycols, Poloxomer polymers such as POLOXOMER® 407, PLURONIC® F108, (both available from BASF Corporation), alkyl polyglycoside (APG), polysorbate, PEG40, castor oil, menthol, and the like. It is understood that while general attributes of each of the above categories of materials may differ, there may be some common attributes and any given material may serve multiple purposes within two or more of such categories of materials. Preferably, such carrier materials are selected for compatibility with the active ingredients found in magnolia extract or from their synthetic analogue compounds, as well as with other ingredients of the composition.

Flavorants among those useful herein include any material or mixture of materials operable to enhance the taste of the composition. Any orally acceptable natural or synthetic flavorant can be used, such as flavoring oils, flavoring aldehydes, esters, alcohols, similar materials, and combinations thereof. Flavorants include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavorants herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, [alpha]-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA), and mixtures thereof. One or more flavorants are optionally present in a total amount of 0.01% to 5%, optionally in various embodiments from 0.05 to 2%, from 0.1% to 2.5%, and from 0.1 to 0.5%.

Sweetening agents among those useful herein include dextrose, polydextrose, sucrose, maltose, dextrin, dried invert sugar, mannose, xylose, ribose, fructose, levulose, galactose, corn syrup, partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones, and mixtures thereof.

Mouth-feel agents include materials imparting a desirable texture or other feeling during use of the composition.

Colorants among those useful herein include pigments, dyes, lakes and agents imparting a particular luster or reflectivity such as pearling agents. In various embodiments, colorants are operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including FD&C dyes and pigments, talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, and mixtures thereof. One or more colorants are optionally present in a total amount of 0.001% to 20%, for example 0.01% to 10% or 0.1% to 5%.

The oral composition of the present invention may comprise an optional abrasive useful for example as a polishing agent. Any orally acceptable abrasive can be used, but type, fineness, (particle size) and amount of abrasive should be selected so that tooth enamel is not excessively abraded in normal use of the composition. Suitable optional abrasives include silica, for example in the form of precipitated silica or as admixed with alumina, insoluble phosphates, calcium carbonate, and mixtures thereof. Among insoluble phosphates useful as abrasives are orthophosphates, polymetaphosphates and pyrophosphates. Illustrative examples are dicalcium orthophosphate dihydrate, calcium pyrophosphate, calcium pyrophosphate, tricalcium phosphate, calcium polymetaphosphate and insoluble sodium polymetaphosphate.

In some embodiments, the compositions of the present invention optionally comprise a tartar control (anticalculus) agent. Tartar control agents among those useful herein include salts of any of these agents, for example their alkali metal and ammonium salts: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof.

In other embodiments, the oral compositions of the present invention optionally comprise a fluoride ion source, useful, for example, as an anti-caries agent. Any orally acceptable particulated fluoride ion source can be used, including potassium, sodium and ammonium fluorides and monofluorophosphates, stannous fluoride, indium fluoride, amine fluorides such as olaflur (N'-octadecyltrimethylendiamine-N,N,N'-tris (2-ethanol)-dihydrofluoride), and mixtures thereof. One or more fluoride ion sources are optionally present in an amount providing a clinically efficacious amount of soluble fluoride ion to the oral composition.

In further embodiments, the oral compositions of the present invention optionally comprise a saliva stimulating agent useful, for example, in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

In yet other embodiments, the oral compositions of the present invention optionally comprise a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophane, L-lysine, methionine, threonine, levocarnitine and L-carnitine), lipotropics (such as choline, inositol, betaine, and linoleic acid), and mixtures thereof.

In some embodiments, the present invention provides a method of treating conditions associated with the presence of oral bacteria comprising providing an oral composition in accordance with any of the above-described embodiments, and applying the oral composition to the oral cavity of the mammalian subject. In some embodiments, the method comprises repeating the application of the composition multiple times until the desired anti-bacterial and/or anti-inflammatory effects are achieved in the subject.

As referred to herein, "inflammation" of the oral tissue generally refers to a localized protective response elicited by injury or destruction of tissues, which serves to destroy, dilute, or sequester both the injurious agent and the injured tissue. In the acute form, it is characterized by pain, heat, redness, swelling, and loss of function. Chronic inflammation is a slow process and primarily characterized by the formation of new connective tissue. Chronic inflammation is often a continuation of acute inflammation or a prolonged low-grade form of inflammation (such as that associated with periodontitis or gingivitis) and usually causes permanent tissue damage. Histologically, inflammation involves a complex series of events, including dilation of arterioles, capillaries, and venules, with increased permeability and blood flow; exudation of fluids, including plasma proteins, and leukocytic migration into the inflammatory locus. Inflammation corresponds to enhanced levels of proinflammatory cellular mediators, or substances that are released from cells, for example, as the result of the interaction of an antigen with an antibody or by the action of antigen with a sensitized lymphocyte.

In various embodiments, application or contacting is accomplished by rinsing, coating, brushing, or layering using appropriate dressing materials. In some embodiments, contacting also includes incidental contact during eating or chewing. In various embodiments, application of the composition comprises the use of an application device which aids in maintaining the contact time of the anti-inflammatory active ingredient comprising magnolia extract to the target tissue for a sufficient time as to allow the pharmacological inhibition of the elevated production of one or more inflammatory mediators, such as $PGE_2$ and TNF-α.

In certain embodiments, an oral composition is not intentionally swallowed, but rather is retained in the oral cavity for a time sufficient to effect the intended utility. In other embodiments, particularly those where the oral composition is provided in an animal product, such as a pet food, pet food supplement (e.g., a treat), or a chew toy, the oral composition may be ingested at small concentrations which are not harmful to the animal. Preferably, specific materials and compositions to be used in this invention are pharmaceutically- or cosmetically-acceptable.

Some embodiments of the present invention provide a method of enhancing the solubility of at least one of the one or more active ingredients derived from magnolia extract, or a synthetic analogue thereof, the method comprising admixing: an effective amount of polyethylene glycol; at least one of the one or more active ingredients found in magnolia extract, or a synthetic analogue thereof.

Polyethylene glycols (PEGs) are a class of polymers with the general formula $H(OCH_2CH_2)_nOH$. PEGs are also soluble in both water and oils. Although PEGs also have two terminal hydroxyl groups per molecule, their properties are generally influenced by their ether-type oxygen atoms in the backbone. PEGs have electron donating tendency or are generally basic (by Lewis acid definition). In addition, PEGs are somewhat surface active. (e.g. behavior like surfactant).

In some embodiments, the polyethylene glycol is selected from the group consisting of: PEG 200; PEG 300; PEG 400; PEG 600; and PEG 1500.

Some embodiments provide an oral composition comprising: from about 0.05 to about 10% by weight polyethylene glycol; from about 0.05 to about 5% by weight of one or more active ingredients found in magnolia extract or a synthetic analogue thereof; and an orally acceptable carrier.

In some embodiments, the polyethylene glycol is present in an amount from about 0.1% to about 5% by weight; and at least one of the one or more active ingredients found in magnolia extract is present in an amount from about 0.1% to about 3% by weight of the composition.

In some embodiments, at least one of the one or more active ingredients is a magnolia extract. In further embodiments, at least one of the one or more active ingredients is magnolol. In other embodiments, at least one of the one or more active ingredients is honokiol. Still further embodiments provide a composition wherein at least one of one or more active ingredients is tetrahydromagnolol. In some embodiments, at least one of the one or more active ingredients is tetrahydrohonokiol. In other embodiments, at least one of the one or more active ingredients is 5,5'-di-n-butyl-biphenyl-2,2'-diol. In some embodiments, the synthetic analogue is selected from isopropyl magnolol; isobutyl magnolol; and dichlromagnolol.

Some embodiments provide a method of treating a disease or condition of the oral cavity comprising: providing a composition comprising: from about 0.05 to about 10% by weight polyethylene glycol; from about 0.05 to about 5% by weight of at least one of the one or more active ingredients found in magnolia extract or a synthetic analogue thereof, selected from: magnolol, honokiol, tetrahydromagnolol, tetrahydrohonokiol (propylhonokiol), 5,5'-di-n-butyl-biphenyl-2,2'-diol, isopropyl magnolol, isobutyl magnolol, and dichloromagnolol; and an orally acceptable carrier; and applying the composition to the oral cavity of a subject in need thereof. In some embodiments, the composition is applied daily for a period of at least one week.

In some embodiments, the disease or condition of the oral cavity includes a disease or condition of the teeth, oral mucosa, gingiva or tongue. Such diseases or conditions include caries, gingivitis, periodontitis, and cosmetic conditions such as yellowing and malodour.

The invention will be described in greater detail by way of specific examples. The following examples are offered for illustrative purposes and are not intended to limit the scope of the invention in any manner. Those of skill in the art will readily recognize a variety of non-critical parameters which can be changed or modified to yield essentially the same results.

EXAMPLES

Oral compositions having the ingredients listed in the tables below can be prepared by the following method. Sodium fluoride and any other salts are dispersed in water. The humectants e.g., glycerin and sorbitol, are added to the mixture in a conventional mixer under agitation. The resultant mixture is agitated until a homogeneous gel phase is formed. A pigment such as $TiO_2$ is added into the gel phase and any acid or base (e.g., NaOH) required to adjust the pH to 6 to 7. Then organic thickeners, carrageenan, and CMC, are added. These ingredients are mixed until a homogenous phase is obtained. The mixture is then transferred to a high-speed vacuum mixer; where the silica abrasives, and the silica thickener are added. The mixture is then mixed at high speed for from 5 to 30 minutes, under vacuum of from about 20 to 50 mm of Hg, preferably about 30 mm Hg. The flavor oil is weighed and the magnolia extracts or their active ingredients are then added to the flavor oil. The flavor oil and magnolia actives are added to the mixture. Surfactants, such as sodium lauryl sulfate (SLS) are added last. The resultant product is a solublized, stable, efficacious, homogeneous, semi-solid, extrudable paste or gel product.

Example 1

Table 1 (below) describes data demonstrating the effect of polyethylene glycol on the solubility of magnolol and honokiol in liquid formulations.

TABLE 1

| Ingredient | Formula 1A w/w % | Formula 1B w/w % | Formula 1C w/w % | Formula 1D w/w % | Formula 1E w/w % |
|---|---|---|---|---|---|
| PEG 600 | — | 2.61 | — | 2.61 | — |
| Proplyene glycol | — | — | — | — | 2.61 |
| Flavorant | 1.31 | 1.31 | 1.31 | 1.31 | 1.31 |
| Honokiol | 0.65 | 0.65 | — | — | — |
| Magnolol | — | — | 0.65 | 0.65 | 0.65 |
| 25% sodium lauryl sulfate solution | 7.84 | 7.84 | 7.84 | 7.84 | 7.84 |
| Saccharin | 0.39 | 0.39 | 0.39 | 0.39 | 0.39 |
| Sodium fluoride | 0.32 | 0.32 | 0.32 | 0.32 | 0.32 |
| Sorbitol | 23.32 | 23.32 | 23.32 | 23.32 | 23.32 |
| Glycerin | 23.04 | 23.04 | 23.04 | 23.04 | 23.04 |
| Na sulfate | 0.65 | 0.65 | 0.65 | 0.65 | 0.65 |
| Water | 42.48 | 39.87 | 42.48 | 39.87 | 39.87 |
| Total | 100 | 100 | 100 | 100 | 100 |
| Appearance | slightly cloudy | clear | opaque | clear | slightly cloudy |

Example 2

Table 2 (below) describes data demonstrating the effect of PEG 600 on the solubility of honokiol and magnolol in liquid formulations.

TABLE 2

| Ingredient | Formula 2A w/w % | Formula 2B w/w % | Formula 2C w/w % | Formula 2D w/w % |
|---|---|---|---|---|
| PEG 600 | — | 2.67 | — | 2.67 |
| Flavorant | 1.6 | 1.6 | 1.6 | 1.6 |
| Honokiol | 0.67 | 0.67 | — | — |
| Magnolol | — | — | 0.67 | 0.67 |
| 25% sodium lauryl sulphate solution | 8.02 | 8.02 | 8.02 | 8.02 |
| 30% cocamidopropyl betaine solution | 1.67 | 1.67 | 1.67 | 1.67 |
| Saccharin | 0.4 | 0.4 | 0.4 | 0.4 |
| Sodium fluoride | 0.33 | 0.33 | 0.33 | 0.33 |
| Sorbitol | 73.59 | 73.59 | 73.59 | 73.59 |
| Na sulphate | 0.67 | 0.67 | 0.67 | 0.67 |
| Water | 13.05 | 10.38 | 13.05 | 10.38 |
| Total | 100 | 100 | 100 | 100 |
| Appearance | Cloudy | clear | cloudy | slightly cloudy |

Example 3

Table 3 (below) describes data demonstrating the effect of PEG and PG on the uptake and growth inhibition of honokiol in liquid formulations.

TABLE 3

| Ingredient | Formula 3A w/w % | Formula 3B w/w % | Formula 3C w/w % | Formula 3D w/w % |
|---|---|---|---|---|
| Glycerin | 18 | 18 | 18 | 20 |
| Na CMC | 1.1 | 1.1 | 1.1 | 1.1 |
| Carrageenan | 0.4 | 0.4 | 0.4 | 0.4 |
| Titanium Dioxide | 0.5 | 0.5 | 0.5 | 0.5 |
| Sorbitol | 17.8 | 17.8 | 17.8 | 19.45 |
| Water | 34.157 | 33.587 | 32.627 | 30.007 |
| Sodium Saccharin - USP | 0.3 | 0.3 | 0.3 | 0.3 |
| Sodium fluoride | 0.243 | 0.243 | 0.243 | 0.243 |
| Sodium sulphate | — | 0.77 | 1.53 | — |
| Honokiol | 1 | 1 | 1 | 1 |
| Polyethyene glycol 400 | 2 | 2 | 2 | — |
| Propylene Glycol | — | — | — | 3 |
| Flavor | 1 | 1 | 1 | 1 |
| Zeodent 105 | 10 | 10 | 10 | 10 |
| Zeodent 115 | 8.5 | 8.5 | 8.5 | 8.5 |
| Zeodent 165 | 3 | 3 | 3 | 3 |
| Sodium lauryl sulphate-NF | 2 | 1.8 | 2 | 1.5 |
| Total | 100 | 100 | 100 | 100 |
| Uptake (μg/HAP disc) | 342 | 347 | 301 | 251 |
| Growth Inhibition (OD610) | 0.0616 | 0.0904 | 0.0496 | 0.2126 |

Each patent, patent application, and printed publication, mentioned in this patent document is hereby incorporated by reference in its entirety.

As those skilled in the art will appreciate, numerous changes and modifications may be made to the embodiments described herein, without departing from the spirit of the invention. It is intended that all such variations fall within the scope of the claimed invention.

The invention claimed is:
1. An oral composition comprising:
2.61 w/w % PEG 600;

0.65 w/w % of an active ingredient found in magnolia extract or a synthetic analogue thereof, selected from magnolol or honokiol; and an orally acceptable carrier;

wherein the amount of the PEG 600 in the composition is sufficient to enhance the solubility of the active ingredient therein.

2. A composition in accordance with claim 1, having a clear appearance.

3. An oral composition comprising:

2.67 w/w % PEG 600;

0.67 w/w % of an active ingredient found in magnolia extract or a synthetic analogue thereof, selected from magnolol or honokiol; and an orally acceptable carrier;

wherein the amount of the PEG 600 in the composition is sufficient to enhance the solubility of the active ingredient therein.

* * * * *